United States Patent [19]

Denis et al.

[11] Patent Number: 5,472,624
[45] Date of Patent: Dec. 5, 1995

[54] LUBRICATING COMPOSITIONS CONTAINING AN AMINE PHOSPHATE WITH A TERMINAL IMIDE RING

[75] Inventors: Jacques Denis, Charbonnieres les Bains; Jacques Garapon, Lyons; Maurice Born, Nanterre; Francoise Dixmier, Sceaux, all of France

[73] Assignee: Institut Francais du Petrole, Rueil Malmaison, France

[21] Appl. No.: 318,934

[22] Filed: Oct. 6, 1994

[30] Foreign Application Priority Data

Oct. 6, 1993 [FR] France .................................. 93 11987

[51] Int. Cl.$^6$ .............................................. C10M 137/08
[52] U.S. Cl. ................................................ 252/32.5
[58] Field of Search ............................. 252/49.9, 32.5, 252/51.5 A

[56] References Cited

U.S. PATENT DOCUMENTS

| | | | |
|---|---|---|---|
| 3,184,412 | 5/1965 | Lowe et al. | 252/46.7 |
| 3,502,677 | 3/1970 | Le Suer | 252/325 |
| 3,723,460 | 3/1973 | Brannen et al. | 252/49.9 |
| 4,014,803 | 3/1977 | Romine | 252/32.7 R |
| 4,193,883 | 3/1980 | Frangatos | 252/49.9 |
| 4,234,435 | 11/1980 | Meinhardt et al. | 252/51.5 A |
| 4,526,697 | 7/1985 | Cox | 252/49.5 |

FOREIGN PATENT DOCUMENTS

| | | |
|---|---|---|
| 2696747 | 4/1994 | France . |
| 2699551 | 4/1994 | France . |
| 1054093 | 1/1967 | United Kingdom . |
| WO83/03616 | 10/1983 | WIPO . |
| WO85/03709 | 8/1985 | WIPO . |

*Primary Examiner*—Margaret Medley
*Attorney, Agent, or Firm*—Millen, White, Zelano & Branigan

[57] ABSTRACT

Anti-wear and high pressure lubricating compositions with a major proportion of lubricating oil and a minor proportion of at least one amine phosphate containing a terminal imide ring result from the reaction, under conditions for the formation of an amine salt, of at least one phosphate having the general formula (I):

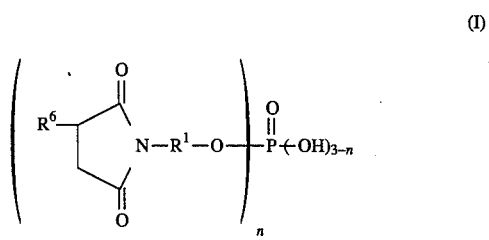

in which n is equal to 1 or 2, $R^1$ is a divalent hydrocarbon group with 1 to 32 carbon atoms, $R^6$ represents a hydrogen atom or a monovalent hydrocarbon group containing usually from 1 to 200 carbon atoms, with at least one amine.

20 Claims, No Drawings

LUBRICATING COMPOSITIONS CONTAINING AN AMINE PHOSPHATE WITH A TERMINAL IMIDE RING

BACKGROUND OF THE INVENTION

The present invention relates to compositions of lubricating oils containing a major proportion of (mineral or synthetic) lubricating oil and a minor proportion of at least one amine phosphate having at least one terminal imide ring.

When the lubrication oils are intended to lubricate parts subjected to high mechanical stresses, a minor proportion of at least one compound, called an antiwear and extreme pressure additive, is usually added to these oils, allowing a considerable reduction in the deterioration of the mechanisms or the tools. Oils containing at least one antiwear and extreme pressure additive are usually used at the level of the distribution into thermal engines, gear systems, bearings or abutments. These added oils are also used during the machining of metals, whether by cutting or shaping. These doped oils or oils with additives, besides their use as engine oils, can also be used as hydraulic fluids and transmission fluids.

SUMMARY OF THE INVENTION

It has now been discovered, unexpectedly, that the amine phosphates described below, some of which have been described by the applicant assignee in the French Patent application filed on Oct. 9, 1992, under the national registration number EN 92/12,277 are good antiwear and extreme pressure additives for the lubricating oils.

In general, the present invention concerns lubricating oils containing a major proportion of lubricating oil and a minor proportion of at least one amine phosphate with a terminal imide ring consisting of a product resulting from the reaction, under conditions for the formation of an amine salt by the neutralization of at least one acid function, of at least one phosphate having the general formula (I) below with at least one amine having the general formula (II) or (III) below. The phosphates have the general formula (I):

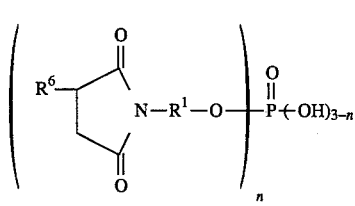

(I)

in which n is equal to 1 or 2, $R^1$ is a divalent hydrocarbon group with from 1 to 32 carbon atoms, $R^6$ represents a hydrogen atom or a divalent hydrocarbon group containing usually from 1 to 200 carbon atoms. Usually, $R^1$ is a divalent, linear or branched saturated aliphatic group. This group most frequently contains from 1 to 18 carbon atoms, and preferably from 2 to 18 carbon atoms, or an aromatic group, optionally bearing substituents such as, for example, alkyl groups, notably lower alkyl groups; this aromatic group most frequently contains from 6 to 24 carbon atoms, and preferably from 6 to 18 carbon atoms. This group $R^1$ is preferably a divalent saturated aliphatic group and most frequently contains from 2 to 16 carbon atoms, and it is either linear or it has branched chains in the form of lower alkyl groups, such as methyl, ethyl, propyl or butyl groups, and preferably methyl or ethyl groups.

The amines used to form the amine phosphates used in the compositions according to the present invention have the general formula (II) or the general formula (III):

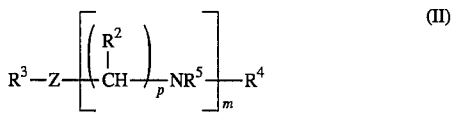

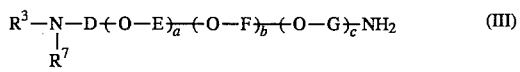

in which each of $R^3$, $R^4$ and $R^5$, which may be identical or different, represents a hydrogen atom or a monovalent hydrocarbon group having from 1 to 60 and preferably from 1 to 48 carbon atoms, Z is selected from the group —O— and —$NR^7$— in which $R^7$ represents a hydrogen atom or a monovalent hydrocarbon group having from 1 to 60 and preferably from 1 to 48 carbon atoms, where $R^3$ and $R^7$ in the formula (III) can combine, along with the nitrogen atom to which they are bound, to form a heterocycle, and each one of the groups $R^2$ independently represents a hydrogen atom or a monovalent hydrocarbon group having from 1 to 4 carbon atoms; when Z is —$NR^7$—, p is a whole number larger than or equal to 2, preferably a number from 2 to 10, and m is zero or a number from 1 to 10; when Z is —O—, p is a whole number larger than or equal to 1, preferably from 1 to 10, and m is a whole number from 1 to 10; each of D, E, F and G, which may be identical or different, represents a divalent hydrocarbon group having from 2 to 6 carbon atoms, a is a whole number from 1 to 60, b and c, which may be identical or different, are equal to zero or to a whole number from 1 to 50, and the sum a+b+c is a whole number from 1 to 60.

Among the amines used most frequently, one can cite those of formula (II) in which m is equal to zero. These monoamines have the general formula $R^3R^4R^7N$, and those in which each of $R^4$ and $R^7$ represents a hydrogen atom and $R^3$ [represents] an alkyl group having from 1 to 32 carbon atoms are frequently used. As examples of these primary monoamines, one can cite methylamine, ethylamine, propylamine, butylamine, pentylamine, hexylamine, heptylamine, octylamine, nonylamine, decylamine, dodecylamine, tetradecylamine, hexadecylamine, octadecylamine, eicosylamine and docosylamine. One can also use a mixture of primary monoamines. Secondary monoamines with formula $R^3BR^4NH$ are frequently used in which each of $R^3$ and $R^4$, which may be identical or different, represents an alkyl group having from 1 to 32 carbon atoms or a mixture of secondary monoamines such as, for example, the cuts of fatty amines with formulas $R^3R^4NH$ whose $R^3$ and $R^4$ groups are monovalent aliphatic $C_8$, $C_{10}$, $C_{12}$, $C_{14}$, $C_{16}$, $C_{18}$, $C_{20}$ or $C_{22}$ hydrocarbon radicals, in the approximate molar proportions given in Table I below. As an example, one can cite the commercial cut Noram 2SH sold by the company CECA, in which $R^3$ and $R^4$ are defined as in the cut P of Table I.

One can also use polyamines with formula (II) in which $R^3$ is a hydrogen atom or a monovalent hydrocarbon group having from 1 to 32 carbon atoms, Z is preferably a —$NR^7$— group in which $R^7$ preferably represents a hydrogen atom or a monovalent hydrocarbon group having from 1 to 32 carbon atoms, where each one of the $R^2$ groups independently represents preferably a hydrogen atom or a methyl group, p is a whole number from 2 to 4, and, when Z is a —$NR^7$— group, m is preferably a whole number from 1 to 5.

Among the compounds with formula (II) mentioned above, one can use those in which Z is —$NR^7$—, $R^3$, $R^2$ and $R^7$ each representing a hydrogen atom, p is equal to 2, and m is a whole number from 1 to 5, or those in which $R^3$ represents a monovalent hydrocarbon group having preferably from 5 to 24 carbon atoms, Z represents a —$NR^7$— group in which $R^7$ is a hydrogen atom, $R^2$ represents a hydrogen atom, p is a whole number from 2 to 4, preferably 3, and m is a whole number from 1 to 5, preferably 1.

The hydrocarbon groups $R^3$ and $R^7$ are usually alkyl, [or] alkenyl groups, which may be linear or branched, aryl groups, arylalkyl (aralkyl) groups, alkylaryl (alkaryl) groups or cycloaliphatic groups. The groups $R^3$ and $R^7$ are preferably linear or branched alkyl or alkenyl groups. The hydrocarbon group $R^2$ is usually an alkyl group, preferably linear, for example methyl, ethyl, n-propyl or n-butyl.

As specific compounds one can cite ethylenediamine, propylenediamine, triethylenetetraamine, tripropylenetetraamine, tetraethylenepentaamine, trimethylenediamine, hexamethylenediamine, 2,2,4-trimethyl- and 2,4,4-hexamethylenediamine, di(trimethylene)triamine, N-alkyl- 1,3-diaminopropane[s], for example, N-dodecyl-1,3-diaminopropane, N-tetradecyl-1,3-diaminopropane, N-hexadecyl-1,3-diaminopropane, N-octadecyl-1,3-diaminopropane, N-eicosyl-1,3-diaminopropane and N-docosyl-1,3-diaminopropane; one can also cite the N-alkyldipropylenetriamines, for example, N-hexadecyldipropylenetriamine, N-octadecyldipropylenetriamine, N-eicosyldipropylenetriamine and N-docosyldipropylenetriamine; one can also cite the N-alkenyl-1,3-diaminopropane[s] and N-alkenyldipropylenetriamines, for example, N-octadecenyl-1,3diaminopropane, N-hexadecenyl-1,3-diaminopropane, N-dodecylenyl[ sic]-1, 3-diaminopropane, N-octadecadienyl-1,3-diaminopropane and N-docosenyl-1,3-diaminopropane. As examples of N,N-disubstituted diamines, one can cite N,N-diethyl-1,2-diaminoethane, N,N-diisopropyl-1,2-diaminoethane, N,N-dibutyl- 1,2-diaminoethane, N,N-diethyl-1,4-diaminobutane, N,N-dimethyl- 1,3-diaminopropane, N,N-diethyl-1,3-diaminopropane, N,N-dioctyl- 1,3-diaminopropane, N,N-didecyl-1,3-diaminopropane, N,N-didodecyl-1,3-diaminopropane, N,N-ditetradecyl-1,3-diaminopropane, N,N-dihexadecyl-1, 3-diaminopropane, N,N-dioctadecyl-1,3-diaminopropane, N,N-didodecyldipropylenetriamine, N,N-ditetradecyldipropylenetriamine, N,N-dihexadecyldipropylenetriamine, N,N-dioctadecyldipropylenetriamine, N-methyl-N-butyl-1,2-diaminoethane, N-methyl-N-octyl-1,2-diaminoethane, N-ethyl-N-octyl- 1,2-diaminoethane, N-methyl-N-decyl-1, 2-diaminoethane, N-methyl-N-dodecyl-1,3-diaminopropane, N-methyl-N-hexadecyl-1,3-diaminopropane [and] N-ethyl-N-octadecyl-1,3-diaminopropane.

As examples of etheramines, one can cite 2-methoxyethylamine, 3-methoxypropylamine, 4-methoxybutylamine, 3-ethoxypropylamine, 3-octyloxypropylamine, 3-decyloxypropylamine, 3-hexadecyloxypropylamine, 3-eicosyloxypropylamine, 3-docosyloxypropylamine, N-(3-octyloxypropyl)-1,3-diaminopropane, N-(3-decyloxypropyl)- 1,3-diaminopropane, (2,4,6-trimethyldecyl)-3-oxypropylamine, N-((2,4,6 -trimethyldecyl)-3-oxypropyl)-1,3-diaminopropane, di(2 -methoxyethyl)amine, di(3-methoxy-n-propyl)amine, di(2-methoxy-2-methylethyl)amine, di(3-ethoxy-n-propyl)amine, di(3-n-propoxy-n-propyl)amine, di(3-n-butoxy-n-propyl)amine, di(3-n-pentoxy-n-propyl)amine, di(3-n-hexyloxy-n-propyl)amine, di(3 -n-octyloxy-n-propyl)amine, di(3-n-nonyloxy-n-propyl)amine, and di(3-n-decyloxy-n-proyl)amine.

It must be understood that it is possible to use as aminated compound one or more compounds having the formula (II) and/or (III). As specific examples of mixtures of compounds with formula (II) one can cite: the cuts of fatty diamines having the formula $R_3$—NH—(—$CH_2$—)$_3$—$NH_2$ whose $R^3$ groups are aliphatic $C_8$, $C_{10}$, $C_{12}$, $C_{14}$, $C_{16}$, $C_{18}$, $C_{20}$ and $C_{22}$ hydrocarbon radicals, in the approximate molar proportions given in Table I below.

TABLE I

| chaines alkyles[1] Coupe[2] | $C_8$ | $C_{10}$ | $C_{12}$ | $C_{14}$ | $C_{16}$ | $C_{18}$ | $C_{18-1}$* | $C_{20}$ | $C_{22}$ |
|---|---|---|---|---|---|---|---|---|---|
| J | 0% | 0% | 0% | 1% | 28% | 71% | 0% | 0% | 0% |
| K | 0% | 0% | 0% | 1% | 5% | 42% | 0% | 12% | 40% |
| L | 3% | 6% | 56% | 18% | 10% | 2% | 5% | 0% | 0% |
| M | 0% | 0% | 0% | 0% | 16% | 4,9% | 79,1% | 0% | 0% |
| N | 0% | 0% | 0% | 2,3% | 31,8% | 24,2% | 39% | 2,7% | 0% |
| P | 0% | 0% | 0% | 0% | 35% | 62% | 3% | 0% | 0% |

*$C_{18-1}$ chain containing one ethylenic double bond.
Key:
[1]Alkyl chains
[2]Cut The polyamines of formulas (III) used most frequently are those in which each of $R^3$ and $R^7$ represents a hydrogen atom, each of D, E, F and G, which may be identical or different, represents an alkylene group having from 2 to 4 carbon atoms, for example ethylene, trimethylene, methylethylene, tetramethylene, methyltrimethylene, 1-methyltrimethylene and 2-methyltrimethylene, a is a whole number from 1 to 60, and b and c are equal to zero, or a is a whole number from 1 to 59, c is equal to zero or to a whole number such that the sum a+ c is equal to 1 to 59, and b is a whole number from 1 to 50; in each case the sum a+b+ c being equal to a whole number from 1 to 60.

As specific compounds with formula (III), one can cite those having the formulas:

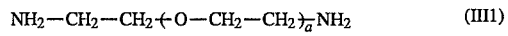

$$NH_2-CH_2-CH_2-(O-CH_2-CH_2)_a-NH_2 \quad (III1)$$

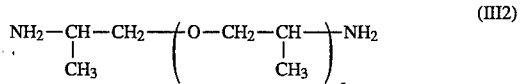

$$NH_2-CH-CH_2-\left(O-CH_2-CH\right)_a-NH_2 \quad (III2)$$
$$\quad\quad\quad | \quad\quad\quad\quad\quad\quad | $$
$$\quad\quad\quad CH_3 \quad\quad\quad\quad\quad CH_3$$

in which a is equal to 2, 3, 5, 6 or approximately 33; and

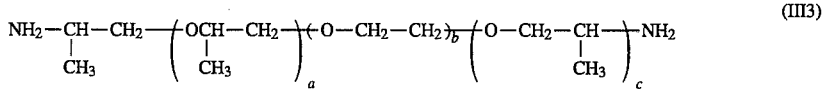

in which b is equal to approximately 8, 9, 15, 16 or 40, and a+ c is equal to approximately 2 or 3.

These products are marketed in particular by the company Texaco Chemical under the name Jeffamine EDR 148 for the product with formula (III1) in which a= 2, Jeffamine D-230 for a product with formula (III2) with a number-average molecular weight of 230, Jeffamine D-400 for a product with formula (III2) with a number-average molecular weight of 400, Jeffamine D-2,000 for a product with formula (III2) with a number-average molecular weight of 2,000, Jeffamine ED-600 for a product of formula (III3) with a number-average molecular weight of 600, Jeffamine ED-900 for a product with formula (III3) with a number-average molecular weight of 900 and Jeffamine ED-2001 for a product with formula (III3) with a number-average molecular weight of 2,000.

The phosphates with general formula (I) are compounds that can be prepared by any method well known to a person skilled in the art. These phosphates can particularly be prepared by the reaction of phosphoric anhydride with formula $P_2O_5$ with an imide alcohol with the general formula (IV):

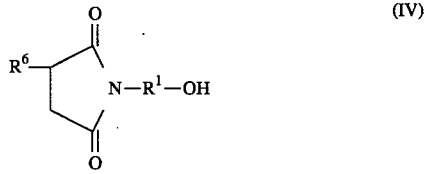

in which $R^1$ and $R^6$ have the definition given above. This imide alcohol of general formula (IV) can be prepared by any method well known to a person skilled in the art. In particular, this compound is the result of the reaction, under the standard conditions for the formation of an imide ring, of an acid, a low alkyl hemiester of this acid (methyl, ethyl, propyl or butyl hemiester) or preferably of a succinic anhydride of formula (V):

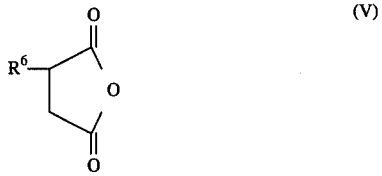

in which $R^6$ has the definition given above, with an amino alcohol with formula HO—$R^1$—$NH_2$ containing a primary amine function and a preferably primary or secondary alcohol function, most frequently a primary alcohol function. This succinic compound usually has a number-average molecular weight of approximately 100–3,000, preferably 200–2,000, and usually 500–1,500. These succinic derivatives have been extensively described in the prior art; they are obtained for example by reacting at least one α-olefin or one chlorinated hydrocarbon with the maleic acid or anhydride. The α-olefin or chlorinated hydrocarbon used for this synthesis can be linear or branched, and they usually contain from 10 to 150 carbon atoms, preferably from 15 to 80 carbon atoms, and most frequently from 20 to 75 carbon atoms in their molecule. This olefin can be an oligomer, for example a dimer, a trimer or a tetramer, or a polymer of a lower olefin, for example one having 2 to 10 carbon atoms, such as ethylene, propylene, 1-n-butene, isobutene, 1-n-hexene, 1-n-octene, 2-methyl-1-heptene or 2-methyl-5-propyl-1-hexene. It is possible to use mixtures of olefins or mixtures of chlorinated hydrocarbons.

As examples of succinic anhydrides used, one can cite succinic anhydride, methylsuccinic anhydride, ethylsuccinic anhydride, propylsuccinic anhydride, n-hexylsuccinic anhydride, n-octadecenylsuccinic anhydride, dodecenylsuccinic anhydride, n-tetradecylsuccinic anhydride and the polyisobutenylsuccinic anhydrides, often called PIBSA, that have a number-average molecular weight as defined before.

As examples of amino alcohols used, one can cite monoethanolamine, 1-amino-3-propanol, 1-amino-2-propanol, 1-amino-4-butanol, 1-amino-2-butanol, 1-amino-5-pentanol, 1-amino-6-hexanol, 1-amino-7-heptanol, 1-amino-8-octanol, 1-amino-10-decanol, 1-amino-11-undecanol, 1-amino-13-tridecanol, 1-amino-14-tetradecanol, 1-amino-16-hexadecanol, 2-amino-2-methyl- 1-propanol, 2-amino-1-butanol and 2-amino-1-pentanol. The amine phosphates used in the compositions according to the present invention can thus be obtained by a method for the preparation consisting of the following steps:

a) at least one amino alcohol with the formula HO—$R^1$—$NH_2$ is reacted with at least one succinic [acid] derivative and preferably a succinic anhydride with formula (V) above, at a temperature of approximately 30° C. to approximately 250° C. under conditions for the formation of the imide ring and elimination of the volatile products (water or alcohol) formed. Usually the reaction is carried out at a temperature of approximately 120° C. to 200° C. with a molar ratio of aminoalcohol to succinic derivative of approximately 0.9:1 to 1.2:1, and preferably approximately 1:1. This reaction can be conducted without any solvent, but preferably a solvent is used, usually one with a boiling point between 30° C. and 250° C., and most frequently between 65° C. and 210° C. The solvent is usually selected so as to allow the elimination of the water and the alcohol formed during the course of the reaction of formation of the imide ring. In particular, a solvent is used that will permit the elimination of the water in the form of a water solvent azeotrope. Usually an organic solvent is used such as, for example, an aromatic or naphthenoaromatic hydrocarbon. More particularly, one can use benzene, toluene, xylenes, ethylbenzene or a hydrocarbon cut such as, for example, the commercial cut Solvesso 150 (190°–209° C.) containing 99 wt % of aromatic compounds. It is possible to use mixtures of solvents, for example a mixture of xylenes. This step a) can in practice be implemented as follows: in a reactor containing the dicarboxylic compound, while the temperature is maintained between 30° C. and 80° C., the amino alcohol is gradually introduced. Then the temperature is raised to 120°–200° C., with elimination of the volatile products (water or alcohols) formed, either by entrainment with a stream of inert gas or by azeotropic distillation with the selected solvent; the dry matter concentration is, for example, 40– 70%, and most frequently it is approximately 50–60%. The duration of the reaction, after the addition of the reagents, is, for example, between 1 and 8 h, and preferably between 3 and 6 h.

b) Either an imide alcohol with the general formula (IV) prepared in step a) diluted in a liquid (preferably a solvent), and preferably one of those which can be used in step a), or possibly after having adjusted the dry matter concentration, for example to approximately 50 wt %, the imide alcohol solution obtained in step a) is gradually placed in contact with a suspension of phosphoric anhydride in a liquid, which is preferably the same as the one in which the imide alcohol is diluted. The contact is established under standard conditions for the formation of phosphates. This formation of phosphates with the general formula (I) usually is carried out at a temperature of approximately 30° C. to approximately 120° C. The reaction is usually completed after approximately 30 min to approximately 2 h. Although it is possible to use an excess amount of one or the other of these compounds with respect to the stoichiometry, it is usually preferred to remain close to the stoichiometric values, that is, to react approximately 1 mol of phosphoric anhydride per 3 mol of imide alcohol, which avoids the need to remove the excess amount of either one of these compounds. Usually, a mixture of phosphates is produced which contains primarily a phosphate having two free hydroxy groups and one phosphate having one free hydroxy group.

c) The liquid containing the phosphate with the general formula (I), or usually a mixture of phosphates with general formula (I), prepared in step b), one adds slowly at least one amine with the general formula (II) and/or (III), preferably diluted in a liquid, which is most frequently the same as the one used in step b). This addition is done under standard conditions for the formation of salts of amines by partial or complete neutralization of the acid functions of the phosphate or the mixture of phosphates obtained in step b). This formation of the amine phosphate(s) is usually carried out at a temperature of approximately 25° C. to approximately 100° C. The reaction is usually completed after approximately 30 min to approximately 2 h. Although one can use an excess amount of either one of these compounds with respect to the stoichiometry, it is usually preferred to be close to the stoichiometric values, that is, to react approximately one amine function per hydroxy function of the phosphate(s) which one wishes to neutralize, which avoids the need to remove the excess amount of either one of these compounds.

Among these phosphates of amines described above, those are usually used in which the group $R^6$ contains at least 6, preferably at least 8, and most frequently at least 10 or at least 12 carbon atoms. The group $R^6$ is preferably a monovalent, linear or branched aliphatic group. When $R^6$ is a branched aliphatic group, the branches are lower alkyl groups (methyl, ethyl, propyl or butyl, and most frequently methyl or ethyl). Preferably, the group $R^6$ contains a carbon chain having a linear fragment with at least 6 carbon atoms.

The compositions according to the invention contain by weight a major proportion of a lubricating oil and a minor proportion, sufficient to improve the extreme pressure and antiwear properties of said oil, of at least one amine phosphate described above. These compositions usually contain a concentration of amine phosphate of 10–250,000 grams per metric ton grams per thousand kilogram of lubrication oil. The preferred concentrations range from 2,000 to 150,000 grams per thousand kilogram, and most frequently from 10,000 to 50,000/grams per thousand kilogram. This concentration represents usually a concentration of phosphorus from 10 to 25,000 ppm, and preferably from 50 to 5,000 ppm by weight.

These lubrication oils (or greases) can also contain one or more other additives, such as, for example, additives that improve the index of viscosity, additives that lower the flow point, anticorrosion additives, antioxidation additives, antirust additives, antifoaming additives, dispersing additives, friction-reducing additives and additives that are more specifically of the detergent type, with which the phosphates of amines of the invention are compatible.

To formulate the compositions of lubrication oils according to the invention, it is possible to add the additives directly to the oil in a simple mixing operation. It is, however, often advantageous to introduce them in the form of "stock solutions" prepared beforehand in the solvents already mentioned above. The "stock solutions" can contain, for example, 20–60 wt %, and usually approximately 50 wt %, of additives.

The following examples illustrate the invention, but they should in no way be considered limiting. Examples 1–6 illustrate the synthesis of the phosphates of amines.

EXAMPLE 1 a) First step

In a 2-L three-necked flask immersed in an oil bath equipped with stirring by a magnetic bar, a thermometer, an addition ampule [sic; funnel] and a Dean-Stark trap, 266 g n-dodecenylsuccinic anhydride (or 1 mol) and the same weight of xylene are introduced. Through the addition ampule, 61 g of aminoethanol (or 1 mol) diluted in the same quantity of xylene are added slowly. Heating is conducted rapidly at the reflux temperature of the xylene. The reflux is maintained for 3 h. 17.5 g of water and 309 g of product, after evaporation of the xylene, are collected. This product is analyzed by infrared spectrometry and proton NMR. The IR spectra contains large bands at 1400 and 1717 cm$^{-1}$, which are characteristic for the imide group, and an intense band at 3450 cm$^{-1}$, which is characteristic of a hydroxy group. The NMR spectrum presents the expected peaks at the requisite intensities, corresponding to the dodecenylsuccinimide of aminoethanol.

b) Second step

In a 2-L three-necked flask, 47.3 g of phosphoric anhydride (⅓mol) suspended in the same weight of xylene are introduced. The imide alcohol, obtained in the first step, diluted in the same weight of xylene, is added slowly through the addition ampule under an argon atmosphere to avoid the hydration of the phosphoric anhydride. When the two reagents are completely dissolved at ambient temperature, the solution is heated slightly (at 60° C. in an oil bath) for 45 min. The product is a homogeneous liquid product, which is analyzed by infrared spectroscopy and proton NMR. The IR spectrum shows the appearance of a broad band at approximately 1010 cm$^{-1}$ corresponding to the P—O—C vibration. The proton NMR allows one to see the chemical shift of the protons of the phosphates at 9 ppm. The acidity of the product is measured using a potash solution. The first acidity corresponds to 102.9 g of potash per kilogram product, and the second acidity corresponds to 204.5 g of potash.

c) Third step

To the product of the second step, 555 g (or 1 mol) of a cut of secondary fatty amines with formula $R^3R^4NH$ where $R^3$ and $R^4$ are defined as in the case of the cut P of Table I, diluted in the same weight of xylene, are added slowly through the addition ampule. This addition allows a complete neutralization of the acid functions of the mixture of product obtained in step b). By a slight heating, to approximately 50° C., and with stirring, for 30 min, a liquid is obtained after evaporation of the xylene which solidifies at ambient temperature and is analyzed by IR spectrometry and NMR spectrometry. The IR spectrum resembles the spectrum of the product of the second step. On the NMR spectrum, one observes an increase in the number of $CH_2$ and $CH_3$ protons due to the protons of the amines. The analysis of the phosphorus NMR spectra allows a verification that only amine phosphates are produced, with very few polyphosphates. The product obtained, diluted to 50 wt % in xylene, is called additive 1.

EXAMPLE 2

The first, second and third steps of Example 1 are started again, replacing in the first step the n-dodecenylsuccinic anhydride by tetrapropenylsuccinic anhydride. The product obtained, diluted to 50 wt % in xylene, is called additive 2.

EXAMPLE 3

The first and second steps of Example 1 are repeated, replacing the n-dodecenylsuccinic anhydride by polyisobutenesuccinic anhydride (PIBSA) (the assay of the anhydride functions of this product shows that there are 0.78 anhydride function per kilogram (kg)) in the same apparatus with stoichiometric quantities of anhydride (1 mol) and aminoethanol (1 mol). The third step is conducted under the same conditions as those described in Example 1 using the same cut of amine in the same proportions. The product obtained, diluted to 50 wt % in xylene, is called additive 3.

EXAMPLE 4–6

The procedure described in Examples 1–3 is repeated. During step c) 277.5 g (or 0.5 mol) of a cut of secondary fatty amines with formula $R^3R^4NH$ corresponding to the cut P of Table I, diluted with the same weight of xylene, are added slowly through the addition ampule. This addition allows a partial neutralization of the acid functions of the product mixture obtained in step b) (neutralization of the first acidity).

The products obtained, diluted to 50 wt % in xylene, are called additives 4, 5 and 6.

EXAMPLE 7

The additives prepared in Examples 1–6 above are evaluated to determine their extreme pressure and antiwear properties in a lubricating oil. The mineral oil used is a 100 [SSU] neutral [oil] with the following main characteristics Kinematic viscosity at 40° C.: 19.1 mm²/sec Kinematic viscosity at 100° C.: 4.01 mm²/sec Index of viscosity: 107

Flow point: −15:° C.

Sulfur content: 0.6 wt %.

The additives are added in the 100 neutral oil to obtain a concentration expressed in phosphorus given in Table II below. The tests are performed on a four-ball apparatus according to the standard ASTM D-2783. The results are indicated in Table II below. One notes that the compositions with additives according to the present invention have better antisiezing properties and better antiwear and extreme pressure properties than the oil alone.

TABLE II

| PRODUITS[1] | TENEUR EN PHOSPHORE PPM DANS L'HUILE[2] | CHARGE DE GRIPPAGE daN[3] | CHARGE DE SOUDURE daN[4] | INDICE CHARGE/ USURE daN[5] | DIAMETRE D'USURE EN mm[6] APRES 1 HEURE SOUS: | | |
|---|---|---|---|---|---|---|---|
| | | | | | 40 daN | 60 daN | 80 daN |
| | 0 | 50 | 126 | 22,2 | 1,07 | 2,08 | 2,32 |
| ADDITIF 1[7] | 780 | 63 | 130 | 25.8 | 0,58 | 2,01 | 2,25 |
| ADDITIF 2[7] | 780 | 80 | 130 | 27,0 | 0,36 | 0,51 | 2,30 |
| ADDITIF 3[7] | 220 | 50 | 160 | 22,4 | 1,03 | 2,02 | 2,27 |
| ADDITIF 3[7] | 506 | 50 | 160 | 22,3 | 1,05 | 2,01 | 2,25 |
| ADDITIF 4[7] | 780 | 50 | 160 | 22,7 | 0,48 | 1,73 | 2,30 |
| ADDITIF 5[7] | 700 | 63 | 160 | 27,1 | 0,42 | 0,45 | 2,22 |
| ADDITIF 6[7] | 220 | 50 | 190 | 24,7 | 0,94 | 1,80 | 2,02 |
| ADDITIF 6[7] | 506 | 50 | 240 | 26,4 | 0,64 | 1,95 | 2,30 |

Key:
[1]Products
[2]Phosphorus content, ppm, in oil
[3]Seizing load, daN
[4]Welding load, daN

We claim:

1. A lubricating oil containing a major proportion of lubricating oil and a minor proportion of at least one amine phosphate with a terminal imide ring consisting of a product resulting from the reaction, under conditions for the formation of an amine salt by the neutralization of at least one acid function, of at least one phosphate having the general formula (I):

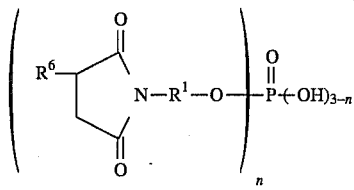
(I)

in which n is equal to 1 or 2, $R^1$ is a divalent hydrocarbon group having from 1 to 32 carbon atoms, $R^6$ represents a hydrogen atom or a hydrocarbon group having usually from 1 to 200 carbon atoms, with at least one amine having the general formula (II) or (III):

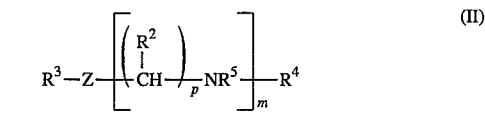
(II)

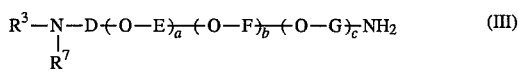
(III)

in which each of $R^3$, $R^4$ and $R^5$, which may be identical or different, represents a hydrogen atom or a hydrocarbon group having from 1 to 60 carbon atoms, Z is selected from the groups —O— and —NR$^7$—, in which $R^7$ represents a hydrogen atom or a hydrocarbon group having from 1 to 60 carbon atoms, $R^3$ and $R^7$ can combine to form, along with the nitrogen atom to which they are connected, a heterocycle, each one of the groups $R^2$ represents independently a hydrogen atom or a hydrocarbon group having from 1 to 4 carbon atoms; when Z is —NR$^7$—, p is a whole number which is larger than or equal to 2, and m is equal to zero or to a number from 1 to 10; when Z is —O—, p is a whole number larger than or equal to 1, and m is a whole number from 1 to 10; each of D, E, F and G, which may be identical or different, represents a divalent hydrocarbon group having from 2 to 6 carbon atoms, a is a whole number from 1 to 60, b and c, which may be identical or different, are equal to zero or to a whole number from 1 to 50, and the sum a+ b+ c is a whole number from 1 to 60.

2. A composition according to claim 1, in which the phosphate used has the general formula (I), in which $R^1$ is a divalent saturated aliphatic group, which is linear or branched and contains from 1 to 18 carbon atoms, or an unsubstituted or alkyl substituted aromatic group having from 6 to 24 carbon atoms.

3. A composition according to claim 1, in which the phosphate used has the general formula (I), in which $R^1$ is a divalent saturated aliphatic group containing from 2 to 16 carbon atoms, which is either linear or branched, with branches in the form of methyl, ethyl, propyl or butyl groups.

4. A composition according to claim 1 in which the group $R^6$ represents a linear or branched aliphatic group having at least 6 carbon atoms.

5. A composition according to claim 1 in which the amine used is an amine with the general formula (II), in which m is equal to zero, Z represents a —NR$^7$— group in which $R^7$ represents a hydrogen atom, $R^3$ represents an alkyl group having from 1 to 32 carbon atoms, $R^4$ represents a hydrogen atom or an alkyl group having from 1 to 32 carbon atoms.

6. A composition according to claim 1 in which the amine used is an amine with the general formula (II), in which m is a whole number from 1 to 10, p is a whole number equal to or larger than 1, Z is —O—, each of $R^3$, $R^4$ and $R^5$, which may be identical or different, represents each a hydrogen atom or a hydrocarbon group having from 1 to 48 carbon atoms, and each one of the groups $R^2$ independently represents a hydrogen atom or a hydrocarbon group having from 1 to 4 carbon atoms.

7. A composition according to claim 1 in which the amine used is an amine with the general formula (II), in which m is a number from 1 to 10 and Z is a —NR$^7$— group in which $R^7$ represents a hydrogen atom or a hydrocarbon group having from 1 to 32 carbon atoms.

8. A composition according to claim 1, in which the amine used is an amine with the general formula (III) in which each of $R^3$ and $R^7$ represents a hydrogen atom, each of D, E, F and G, which may be identical or different, represents a divalent hydrocarbon group having from 2 to 4 carbon atoms, a is a whole number from 1 to 60, and b and c are equal to zero, or a is a whole number from 1 to 59, c is equal to zero or to a whole number such that the sum a+c is from 1 to 59, and b is a whole number from 1 to 50, the sum a+ b+ c being in all cases a whole number from 1 to 60.

9. A composition according to claim 1, containing a sufficient amount to improve the extreme pressure and antiwear properties of said oil of said at least one amine phosphate.

10. A composition according to claim 9, containing from 10 to 250,000 grams per thousand kilogram of said at least one amine phosphate.

11. A composition according to claim 10, containing from 2000 to 150,000 grams per thousand kilogram of said at least one amine phosphate.

12. A composition according to claim 4, wherein $R^6$ is an aliphatic group containing at least 8 carbon atoms.

13. A composition according to claim 5, wherein $R^4$ is said alkyl group of 1–32 carbon atoms.

14. A composition according to claim 7, wherein $R^7$ is hydrogen or a linear or branched alkyl or alkenyl group.

15. A composition according to claim 5, in which the group $R^6$ represents a linear or branched aliphatic group having at least 6 carbon atoms.

16. A composition according to claim 6, in which the group $R^6$ represents a linear or branched aliphatic group having at least 6 carbon atoms.

17. A composition according to claim 7, in which the group $R^6$ represents a linear or branched aliphatic group having at least 6 carbon atoms.

18. A composition according to claim 8, in which the group $R^6$ represents a linear or branched aliphatic group having at least 6 carbon atoms.

19. A composition according to claim 18, in which the phosphate used has the general formula (I), in which $R^1$ is a divalent saturated aliphatic group containing from 2 to 16 carbon atoms, which is either linear or branched, with branches in the form of methyl, ethyl, propyl or butyl groups.

20. A composition according to claim 19, wherein $R^6$ is an aliphatic group containing at least 8 carbon atoms.

* * * * *